United States Patent [19]

Vitale

[11] Patent Number: 5,135,922
[45] Date of Patent: Aug. 4, 1992

[54] PREVENTION AND TREATMENT OF MICROBIAL INFECTION BY PHOSPHOGLYCERIDES

[75] Inventor: Joseph J. Vitale, Weymouth, Mass.

[73] Assignee: Med-Tal, Inc., Weymouth, Mass.

[21] Appl. No.: 579,242

[22] Filed: Sep. 4, 1990

Related U.S. Application Data

[63] Continuation of Ser. No. 366,475, Jun. 15, 1989, abandoned, which is a continuation-in-part of Ser. No. 142,522, Jan. 7, 1988, abandoned, which is a continuation-in-part of Ser. No. 75,556, Jul. 20, 1987, abandoned, which is a continuation-in-part of Ser. No. 891,880, Jul. 30, 1986, abandoned, which is a continuation-in-part of Ser. No. 620,886, Jun. 15, 1984, abandoned.

[51] Int. Cl.[5] ............................................ A61K 31/685
[52] U.S. Cl. ........................................ 514/78; 514/76; 514/77; 514/167
[58] Field of Search ................... 514/167, 78, 76, 77

[56] References Cited

U.S. PATENT DOCUMENTS 4,221,784  9/1980  Growdon et al. .................... 514/78
4,666,893  5/1987  Tsuchiya ............................... 514/48

FOREIGN PATENT DOCUMENTS 100964  2/1984  European Pat. Off. .

OTHER PUBLICATIONS

Merck Index, p. 711, No. 5287, 1976.
Ngwenya et al. Biochem & Biophy Acta 839:9-15, 1985.
Zeisel; Lecithin Chop. 14, pp. 323-345, Wash. D.C., Am Oil Chim Soc. 1985.

*Primary Examiner*—John W. Rollins
*Attorney, Agent, or Firm*—Lahive & Cockfield

[57] ABSTRACT

Phosphoglycerides are effective therapeutic and prophylactic agents for bacterial, yeast protistan and viral infections. This invention discloses use of these phosphoglycerides in a variety of therapeutic contexts. Therapeutic methods of this invention pertain to use of phosphoglycerides to combat bacterial, yeast protistan, and viral infections. Phosphoglycerides can be used in therapy and in prophylaxis of AIDS patients. A preferred phosphoglyceride is a species of phosphatidylcholine in which linoleic acid is the primary fatty acid constituent.

11 Claims, 5 Drawing Sheets

PREVENTION AND TREATMENT OF MICROBIAL INFECTION BY PHOSPHOGLYCERIDES

This is a continuation of co-pending application Ser. No. 07/366,475 filed on Jun. 15, 1989 which is a continuation-in-part of 142,522, Jan. 7, 1989 which is a continuation-in-part of 075,556 Jul. 20 1987, which is a continuation-in-part of 891,880 Jul. 30, 1986 which is a continuation-in-part of 620,866 Jun. 15, 1984 now abandoned.

FIELD OF THE INVENTION

This invention is in the field of antimicrobial chemotherapy and pertains to a method of preventing or treating infectious disease.

BACKGROUND OF THE INVENTION

Group B Streptococci (GBS) are a major cause of morbidity and mortality in neonates and in other patients with compromised host defense mechanisms. The importance of GBS disease for newborn infants in the United States was underscored in an NIH sponsored workshop on Group B Streptococcal Infection. Fisher, G. S. (1983) *J. Infect. Dis.* 148, 163–166.

The incidence of GBS disease is estimated at between 2 to 5 cases per 1000 live births. Pass, M.A. (1979) *J. Pediatr.* 795, 437–443. At highest risk are premature infants, whose birth weight is less than 2500 grams and infants born to mothers with premature rupture of membranes. Fisher, G. W., supra. Susceptibility to and severity of GBS disease has been associated with several risk factors including deficient or altered host defense mechanisms. Hill, H. R. et al. (1979) *Pediatrics* 64, 5787-5794. Studies have shown that human neonates who develop Group B Streptococcal Sepsis usually lack opsonic antibody to their infecting strain. Opsonic antibody is antibody that combines with antigen and facilitates ingestion of the antigen by phagocytes. In addition, these neonates usually have impaired polymorphonuclear leukocyte (PMN) function. Hemming, V. G. et al. (1976) *J. Clin. Invest.* 58, 1379–1387; Shigeoka, A. S. et al. (1979) *J. Pediatr.* 95, 454-460.

Despite aggressive supportive therapy and early institution of appropriate antimicrobial agents, the mortality rate for early-onset Group B Streptococcal Disease continues to be in the 25-75% range. This observation has prompted considerable interest and research in the development and use of adjunctive treatment modalities, which focus on improving the host's immune status, including a vaccine for maternal immunization [Baker, C. J. et al. (1978) *J. Clin. Invest.* 61, 1107–1110]; the use of ante and intrapartum prophylactic antibiotics; and various blood components including: whole blood, polymorphonuclear leukocytes, and immune serum globulins modified for intravenous use. However, despite such investigative work with animal models of disease, the mechanisms of host resistance to GBS have not been clearly defined. Some strains of GBS appear to be more virulent than others. Furthermore, all GBS strains are not uniformly susceptible to the action of antibody and complement.

Susceptibility to GBS disease, like to other infectious diseases, is multi-factorial and impinges on native and acquired immunity which are influenced by the host's genetic constitution, sex, age, and nutritional status. Of the aforementioned factors, there is very little information available as to the role of single or aggregate nutrients on host resistance to GBS disease. Almost any nutritional deficiency or excess may affect adversely one or more components of the immune system. Conversely the same nutrients that impinge on the immune system may also be essential for the multiplication and virulence of certain pathogenic microorganisms.

The need for a safe and effective regimen for preventing GBS infection in newborns was made evident in a recent editorial, "Prevention of Early-Onset Group B Streptococcal Infection in the Newborn" (1984) *Lancet* 1, 1056-1058. In evaluating one potential regimen, antibiotic prophylaxis, the author concluded that firm recommendations as to its use must await further experimentation.

DISCLOSURE OF THE INVENTION

This invention pertains to a method of therapy or prophylaxis of bacterial, yeast, protozoan and viral infections and to novel compositions comprising essentially pure phosphatidyl choline containing only omega-6 fatty acids, particularly only linoleic acid. The method comprises administering, in either therapeutic or prophylactic amounts, one or more of the phosphoglycerides: phosphatidylcholine (lecithin) preferably phosphatidycholine containing linoleic acid, phosphatidylethanolamine, phosphatidylserine or phosphatidylinositol.

The method of this invention is founded upon the discovery that the phosphatidylcholine (PC)—an ubiquitous constituent of biomembranes—protects newborn animals against mortality which usually results from Group B hemolytic Streptococcal infection. As explained, this microorganism is particularly virulent in newborns. In an experimental model of neonatal sepsis in which Group B hemolytic streptococci (GBS) was the causative agent, phosphatidylcholine proved an effective therapeutic agent. PC treatment prevented or delayed the death of newborn rats inoculated with GBS. A single injection of PC significantly increased the number of newborn rats which survived GBS inoculation and significantly prolonged the mean survival time of the entire treated group.

PC was also effective in prophylaxis, that is prevention, of GBS infection. When PC was given prophylactically to pregnant rats, PC reduced mortality in their offspring inoculated with GBS. Moreover, PC prevented weight loss in post-natal rats by enhancing host defense mechanisms.

In view of these findings, phosphatidylcholine may have a role as a nutritional supplement or as a practical therapeutic agent, or adjunct, in the treatment and prevention of GBS disease and other infections (e.g. viral, fungal, protistan etc.). In principle, other phosphoglyceride constituents of biomembranes are likely to act similarly. Thus, the phosphoglycerides phosphatidylethanolamine, phosphatidylserine and phosphatidylinositol may also be useful in combating or preventing bacterial infection. Also, because the phosphoglycerides may act by stimulating the hosts immune response to foreign organisms in general, they may be effective therapeutic and prophylactic agents for viral infection.

PC and possibly other phosphoglyceride components of biomembranes are believed to protect against the lethal action of bacteria by promoting the clearance of these disease-causing organisms by the reticuloendothelial system (RES) by altering the fluidity, and consequently the function, of the phagocytic cells (i.e., the polymorphonuclear leukocytes and macrophages) which make up the RES. This theory is supported by a study involving oral ingestion by humans of species of phosphatidylcholine in which linoleic acid was the primary fatty acid constituent (e.g., soy phosphatidylcholine). The study revealed that the composition and the concentration of arachidonic acid in polymorphonuclear leukocytes from these humans had been modified. This alternation in membrane lipid composition was found to occur in conjunction with an increased immune response.

BEST MODE OF CARRYING OUT THE INVENTION

Figure 1:
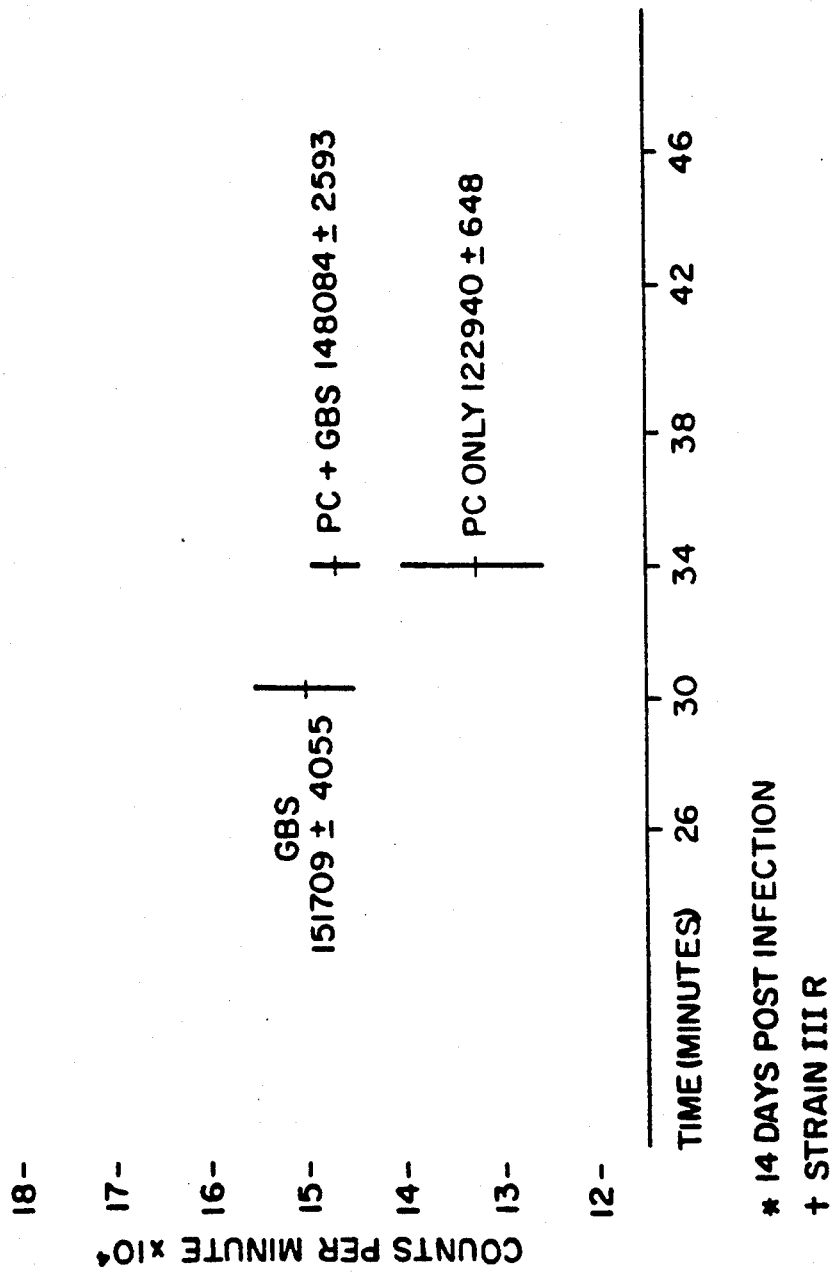
FIG. 1 illustrates the opsono-phagocytic activity of PC-treated and untreated neonatal rats infected with GBS.

Animal experiments indicate that biomembrane phospholipid phosphatidylcholine (PC) is an effective therapeutic and prophylactic agent for bacterial, yeast and viral infections. The therapeutic efficacy of PC was evaluated in an experimental model of neonatal sepsis. Sepsis was induced in neonatal rats with a type III GBS strain resistant to opsonization. After infection, newborn rat pups were randomly assigned to receive equal volumes of either saline (controls) or 5 mg of PC. For a period of 30 days after administration of the phospholipid, animal mortality was observed. All 35 control animals died. In contrast, six out of thirty-three (18%) of the animals that received PC survived. In addition, the cumulative mean survival time was significantly increased in the PC treated group when compared to the controls (26 hrs vs 12 hrs).

Prophylactic efficacy of PC was evaluated by administering PC to pregnant rats prior to parturition and then inoculating offspring with GBS. The survival rate of pups delivered by PC-treated mothers was greater than pups delivered by mothers that did not receive PC. (23% of pups from PC-treated mothers survived whereas only 2.5% of pups from untreated mothers survived for 72 hours after infection.) PC also prevents vertical transmission of GBS from mother to fetus. Neonates of infected dams treated with PC were less likely to be bacteremic, that is, harbor viable GBS organisms in their tissues.

Because PC is an integral part of biomembranes, two mechanisms of action might be proposed. PC might modulate host immune response by stimulating the phagocytic function of polymorphonuclear leukocytes (PMNLs) and macrophages. Phagocytosis is probably influenced by membrane fluidity. Because membrane fluidity depends upon its composition, PC, a major membrane component, may modify fluidity, and, in turn, phagocytosis. Together with reticular cells and other phagocytic cells, PMNLs and macrophages, make up the reticulo-endothelial system (RES) a "scavenger" system which traps, ingests and degrades invading organisms. Thus, by stimulating the component cells of the RES, PC may promote clearance of foreign organisms from host tissues by the RES. Countering this hypothesis are some observations that simple lipid complexes (cholesterol, oleate, ethyl stereate, and methyl palmitate) markedly depress the functional activity of the RES.

PC may also act by modifying surface components of the bacteria. These modifications may result in increased phagocytic uptake of invading organisms by host phagocytic cells or they may result in an abatement of the virulence of micro-organisms.

As determined by a chemiluminescence test for assessing opsono-phagocytic activity of phagocytic blood cells, PC-treated animals infected with GBS have a blunted opsono-phagocytic activity. This could mean that PC masks or alters the immunogenic surface receptors of the injected GBS and this results in a diminished type specific antibody response to the organism. Alternatively, PC may have a paradoxical effect of improving PMN function on the one hand and of decreasing B cell function and antibody production on the other hand. A role for PC in the inhibition of lectin mediated blastogenesis has been previously proposed. Chen, S. S. and Keenan, R. M. (1977) *Biochem. Biophys. Res. Comm.* 79, 852–858.

As discussed above, in an experimental model of Group B Streptococcal Disease, phosphatidylcholine offered protection against a virulent Group B Streptococcal strain. Interestingly, these results resemble the results of previous studies employing blood components to protect such animals from Group B Streptococcal Infection. See e.g., Santos, J. I. et al. (1980) *Pediatr. Res.* 14, 1408–1410. However, because PC has no inhibitory effect on GBS in vitro and actually sustains GBS growth in culture, it is reasonable to speculate that PC enhances the immune response of the newborn animal to GBS.

The effects of phosphatidylcholine on the immune system—which is described herein for bacterial and yeast (Example 7) infections—supports the use of phosphoglycerides as a method of therapy and prophylaxis for viral infections, as well.

Phosphatidylcholine belongs to a family of phosphoglycerides which are found almost entirely in cellular membranes as constituents of the lipid bilayer. Phosphoglycerides comprise glycerol phosphate, two fatty acid residues esterified to the hydroxyl groups at carbons 1 and 2 of glycerol and an alcohol component (e.g. choline in phosphatidylcholine) whose hydroxyl group is esterified to the phosphoric acid. Because of the similarity of structure and function of these compounds, the therapeutic and protective action manifested by PC toward bacterial infection may be common to the group. This is believed to be so particularly for the other major phosphoglycerides, phosphatidylethanolamine, phosphatidylserine and phosphatidylinositol.

A preferred embodiment of this invention employs a species of phosphatidylcholine in which linoleic acid (C18:2n-6) is the primary (preferably the only) fatty acid constituent (e.g. soy phosphatidylcholine). Linoleic acid is an omega-6 fatty acid, as opposed to an omega-3 fatty acid (e.g. marine oils) and is an essential dietary nutrient, because it cannot be synthesized by mammals but must be obtained from plants. Because linoleic acid is the major lipid consumed in conventional Western diets, it is the major fatty acid comprising the phospholipid bilayer of the cell membranes of most people who consume a Western diet. The phosphatidylcholines containing omega-6 fatty acids can be synthesized by adding or replacing fatty acids on carbons 1 and 2 of the glycerol molecule. For example, fatty acids on carbons 1 and 2 of a glycerol molecule can be removed and the phospholipid can be reconstituted in the presence of linoleic acid. In addition, phosphatidylcholines containing omega-6 can be isolated from heterogenous preparations of phosphatidylcholines available from commercial sources.

A study, which is described in greater detail in Example 7, revealed that in response to a dietary supplement providing a minimum of 18 gms of phosphatidylcholine containing linoleic acid as the primary fatty acid constituent, but not in response to a placebo, PMNL phospholipid arachidonic acid (C20:4n-6) content increased. In addition, stimulation of these PMNLs with Candida albicans resulted in phospholipid arachidonic acid release which correlated with PMNL killing and phagocytosis of the yeast. Further, when these PMNLs were exposed to a calcium ionophore or N-formyl-methionyl-leucylphenylalanine, the amount of leukotriene B4 (LTB4), an immunosuppressor increased substantially.

In constrast, neutral fats providing equivalent amounts of linoleic acid appeared to have no effect on PMNL function or PMNL fatty acid composition. This difference between linoleic acid contained in phospholipids and linoleic acid contained in neutral fat is likely related to the way the body metabolizes and utilizes linoleic acid from the two different sources. Scrow, R. O., Stein Y. and Stein L., *J. Biol. Chem.*, 242: 4919-24 (1967); Borgstrom B., *Gastroenterology*, 78: 954-64 (1980).

For example, phospholipids, although comprising only 5-9% by weight, form 40-65% of the outer surface of chylomicrons. Davenport, H. W. *Physiology of the Digestive Tract*, p. 218 et seq., Year Book Medical Publishers, Chicago (1982). This enables an easy exchange of phospholipids with the lipophilic cellular membranes with which they contact. Neutral fats, on the other hand, are carried mainly in the triglyceride-rich core and cannot exchange as easily.

The phosphoglycerides may be administered enternally or parenterally. Enteral administration is the preferred route. As the phosphoglycerides are components of many foods, they may be administered conveniently by ordering a diet which will supply the appropriate amount of the phosphoglycerides. Alternatively, the phospholipid may be given alone in bolus doses as a dietary supplement.

In situations of acute need, it may be desirable to give the phosphoglycerides parenterally, preferably by intravenous infusion. Pharmaceutical compositions may be prepared comprising the phosphoglyceride in a physiologically-acceptable vehicle. For example, a sterile emulsion of the phosphoglycerides in phosphate buffered saline is a suitable composition for infusion. In general, dosage regimens may be optimized according to established principles of pharmacokinetics.

As a therapeutic agent, the phosphoglycerides may be administered to a patient who has been determined clinically to have contracted a bacterial, yeast or viral infection. Besides being efficacious therapeutic agents in their own right, the phosphoglycerides may be useful adjuncts to conventional therapeutic regimens. For example, phosphatidylcholine may be administered conjunctively with antibiotics or other anti-microbial agents.

Prophylactic use of the phosphoglycerides is appropriate in patients who are at risk of contracting bacterial infection. Patients especially susceptible to bacterial infection include premature infants, infants born to mothers with prematurely ruptured membranes and persons whose immune system is suppressed or compromised such as certain cancer patients (e.g. leukemics) or cancer patients undergoing chemotherapy, persons suffering from Acquired Immune Deficiency (AIDS) or the aged. In prophylaxis, the phosphoglycerides may be administered alone or as an adjunct to other forms of prophylaxis. In particular, the phosphoglycerides can be be used with other prophylaxis forms in the treatment of AIDS. Vitamin D3 or its active metabolites such as the hormonal product, 1,25-$(OH)_2$ D3, (HD) can inhibit Interleukin-2 production and depress T-cell proliferation when T-cells are exposed to mitogen. Normally, receptors for HD are not present on resting T- and B-cells but are present on monocytes and malignant T-lymphocytes. When resting T-cells are exposed to a mitogen, proliferation and differentiation occurs with expression of HD receptors. The addition of HD in pico-molar concentrations inhibits the proliferation of activated T-cells, presumably by inhibiting the growth promoting lymphokine, IL-2. Macrophages as well as T-cells may be infected with the Human-Immunodeficient Virus (HIV). The macrophage is required for T-cell activation and may have an important role not only in promoting the replication of the virus but also in transmitting virus to resting T-cells. By enhancing macrophage function with, for example, phosphatidylcholine treatment and reducing T-cell proliferation by HD administration, a combined therapeutic regimen of both phosphatidylcholine/HD would be of value in mitigating the morbidity associated with the HIV infection.

A important mode of prophylaxis of neonatal sepsis is treatment of the mother with a prophylactic agent prior to parturition. As described above, maternal administration of PC effectively protects newborns against GBS infection. Thus, the phosphoglycerides may be administered prophylactically late in pregnancy, either alone or in conjunction with other prophylactic agents (e.g. antibiotics) in situations of high risk of neonatal infection.

The use of phosphoglycerides to combat or ward off bacterial infection has several advantages. Because phosphoglycerides are common nutrients, there is minimal risk of toxicity attendant to their administration. In addition, as common components of foods, they can be administered orally and may be given therapeutically by prescribing a diet which provides the desired amount.

From a nutritional point of view, PC, in particular, has the potential for being exploited to the benefit of the host. In mammalian tissue free choline participates in four enzyme-catalyzed pathways: oxidation, phosphorylation, acetylation, and base exchange. See Zeigel, S. H. (1981) *Ann. Rev. Nutr.* 1, 95-121. During periods of rapid growth, large amounts of choline are needed for membrane and myelin synthesis. The ultimate source of dietary choline is the phospholipid, lecithin. However, the newborn rat is unable to consume choline-containing foods other than its mother's milk. It may be possible to prophylactically increase the plasma choline concentration in the newborn animal by giving a cholinerich diet or by administering PC via parenteral route to the mothers during pregnancy. Although the placenta is incapable of taking up lecithin from maternal blood and transporting it to the fetus, it does possess both passive and active transport mechanisms which result in significant transport of choline from maternal blood into the placenta. Biezenski, J. et al. (1971) Biochim. Biophys. Acta 230, 92-97.

The invention is further illustrated by the following examples.

EXAMPLES

Example 1

Therapeutic Effect of PC in Neonatal Sepsis

Preparation of Phosphatidylcholine (PC)

Soy lecithin, 95% pure, (Unilever Inc., Valardinger, Netherlands) was mixed in phosphate buffered saline (PBS) to a concentration of 250 mg/ml. This Lecithin preparation contained 25.84 nanomoles of phosphatidylcholine per 100 $\mu$l of mixture as determined by thin layer chromatography.

Preparation of Organisms

A human isolate of Group B Streptococci Type III-R, resistant to opsonization by most antibody containing serum was cultured in Todd Hewitt (Difco Laboratories, Detroit) broth overnight at 37° C., washed, concentrated in phosphate buffered saline (PBS) by centrifugation and adjusted to $1 \times 10^9$ cfu/ml in PBS as previously described. Hemming, V. E., et al. (1976) J. Clin. Invest. 58, 1379-1387.

Neonatal Rat Infections

Sprague Dawley outbred pregnant female rats (Charles River) and Lewis pregnant female rats were obtained one week before delivery. The neonatal progeny less than 24 hours old were randomly assigned to groups and entered into the study. Animals were inoculated intraperitoneally with 0.1 cc of PBS containing $10^4$ streptococci. In the protection studies, the animals also received separate equal volume injections of saline or 25.84 nanamoles of phosphatidylcholine immediately after bacterial inoculation. The rat litters were observed at six hour intervals for mortality. Surviving rats were observed for a total of three weeks as previously described. Santos, J. I., et al. (1980) Pediatr. Res. 14, 1408-1410.

Chemiluminescence Procedure

A chemiluminescence procedure, as modified by Selveraj and co-workers, J. Retic. Endoth. Soc. 31 3-16 (1982), for microquantities of whole blood, was employed in assessing the opsono-phagocytic activity of PC-treated and control Lewis rats that survived GBS challenge. Briefly, approximately 0.5 ml of heparinized whole blood was taken from each rat two weeks post infection. Total WBC and differential counts were determined on each blood sample. The assay was conducted in the following manner: to an 8 ml vial, the following reagents were added: 0.8 ml of KRB buffer, 1.5 ml sterile distilled water, 2.5 ml 1 mM luminol (Kodak), 10 ml whole blood, and finally 150 $\mu$l of an overnight culture of GBS Type III washed and adjusted to $1 \times 10^9$ c.f.u. per ml to achieve a PMN: particle ratio of 1:3000. Blood from each rat was studies in duplicate; thus two samples from each rat were placed in the scintillation counter. Three background samples with the particle and chemiluminescence mixture were run with each assay. The samples were monitored for chemiluminescence using an LKB Rack Beta 1211 Liquid Scintillation counter. Each sample was counted for 5 seconds every 6 minutes. The assay was allowed to run for 30 minutes after which time chemiluminescence activity had peaked and decreased significantly.

Statistical Analysis

Comparison of significance of differences between survival values in the animal studies were performed by use of the Fischer exact test.

Results

The survival rate in 35 unprotected (controls) neonatal Sprague Dawley rats infected with Type III-R, GBS was 0. In contrast, 6/33 (18%) of the rats that received phosphatidylcholine survived (p 0.01). Moreover, the cumulative means survival time was also significantly increased in the PC treated group when compared to the controls (26 hours vs. 12 hours; p 0.01).

Unexpectedly, newborn Lewis rats challenged with the same strain of GBS and randomized to receive either saline (n=34) or PC (n=16) all survived. Differences in animal strain susceptibility were corroborated in several experiments. Sprague Dawley rats were uniformly susceptible and Lewis rats resistant to this GBS strain.

The opsono-phagocytic activity of GBS infected Lewis rats was determined fourteen days post infection using whole blood and un-opsonized live GBS as the particle. Depicted in FIG. 1 are the chemiluminescence (CL) values for rats that were infected and received either saline or PC and uninfected rats that received only PC. Animals that received PC had a lower mean CL response than saline treated controls but both had a greater response than uninfected animals.

Example 2

Prophylactic Effect of PC

The present study was designed to evaluate the prophylactic effect of PC given to pregnant Sprague Dawley dams on GBS infection in their offspring.

Outbred Sprague Dawley rats (Charles River Breeding Laboratory, Wilmington, MA) were used in all experiments. Single doses of 250 mg purified phosphatidylcholine dissolved in 1 cc of 0.9% saline were injected intraperitoneally (i.p.) at time intervals ranging from 120 hours (5 days) to 96 hours (4 days) prior to parturition. Control animals received equal volume i.p. injections of saline. After delivery all of the rat pups ranging in age from 24-36 hours were injected i.p. with $5 \times 10^6$ c.f.u. of GBS and observed for mortality.

Figure 2:
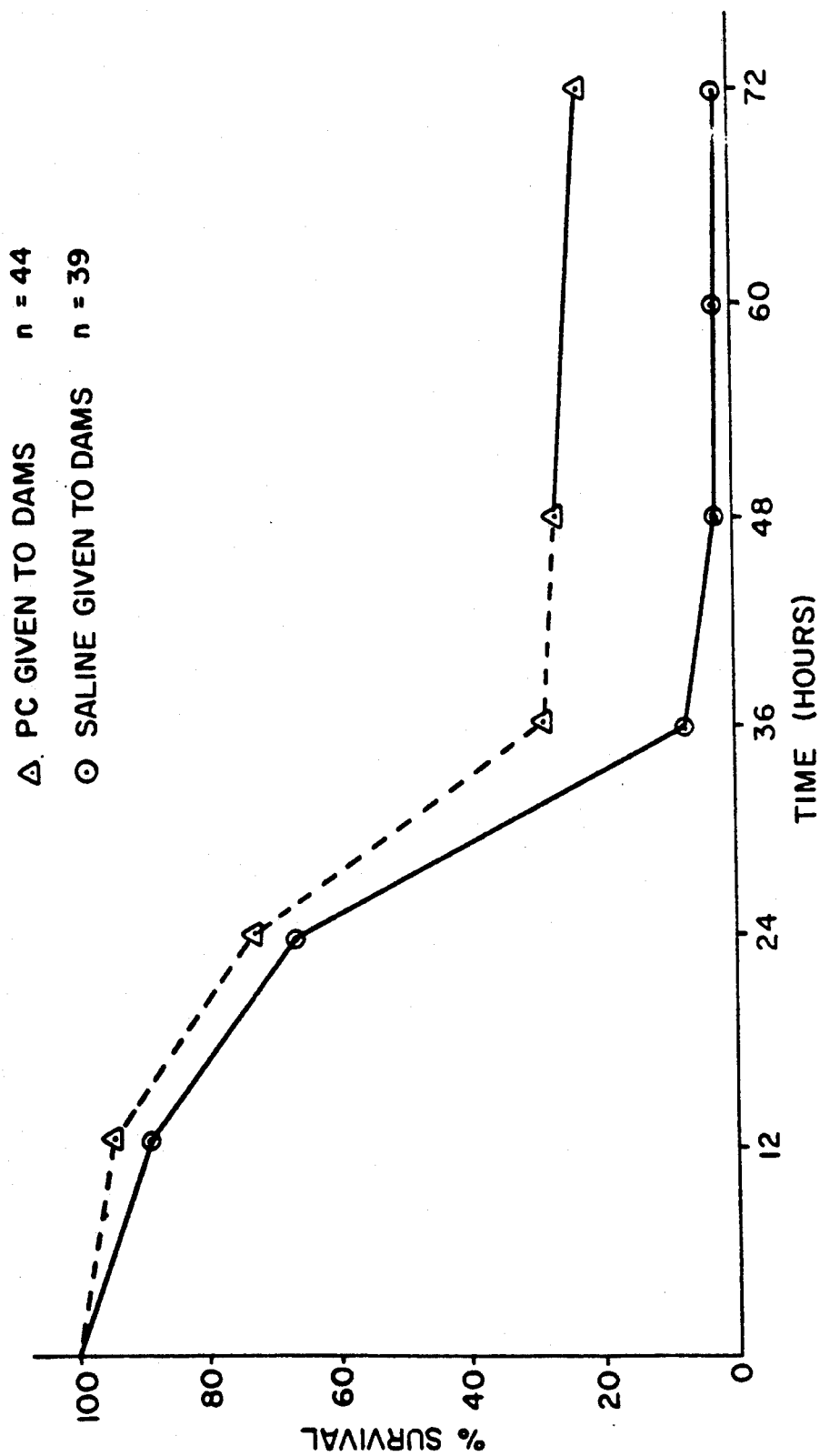
FIG. 2 illustrates the increased survival rate of rat pups whose mothers were treated with PC.

The results presented in FIG. 2 indicated that rat pups whose mothers were treated with PC had an increased survival rate of 10/44 (23%) versus 1/39 (2.5%) for pups born to saline-treated controls. (P<0.05).

In an additional experiment, nineteen pregnant Sprague Dawley rats were randomized to receive 500 mg PC (n=10) or saline (n=9) i.p. on day 16 of gestation. All rats were challenged with $10^9$-$10^{10}$ CFU of GBS type III, 24-48 hours prior to expected delivery.

17/19 (89%) were documented to be bacteremic 24 hours post inoculation. Two PC treated animals and 4 controls died 24-80 hours post inoculation; GBS was isolated from these animals and their unborn pups.

Seventy-four pups were born to 8 PC-treated animals; fifty-one pups to the 5 remaining controls. Pups were sacrificed and cultured at 4–8 hour intervals following birth. GBS was isolated from liver, spleen, blood or brain in 15/74 (20%) pups in PC-treated group. In contrast, 19/51 (37%) of saline treated groups had positive cultures.

These results suggest that prophylaxis with PC, an important component of all biomembranes, may interfere with the vertical transmission of GBS. Further investigation of PC interaction with GBS and with maternal immune function may define its role in the antepartum management of GBS infected mothers.

Example 3

Effect of PC on Postnatal Rats

This Example illustrates that the effect of PC on pre-weaned rats includes weight gains that can be attributed to enhanced host defense mechanisms.

A rat litter (N=13) was randomly assigned to receive either a single i.p. injection of PC soy lecithin (see Example 1, above) or 500 mg/kg of an equivalent control injection of phosphate buffered saline (PBS). Pups were allowed to nurse and weighed every two to three days.

The weight distribution for all animals prior to weaning is given in Table I. All animals had similar weight gain during the first two weeks. Between weeks 2 and 3, however, the PC treated group gained more weight and by 21 days post-injection, the mean weight of the PC-treated group was $39.1 \pm 1.1$ grams versus $24.3 \pm 1.2$ grams for the control group.

Differences in weight can be attributed to enhanced host defense mechanisms in the PC-treated group. Although no visible signs of intercurrent illness was noted for the control group, a sub-clinical infection cannot be ruled out. These results suggest that PC may be used prophylactically as a useful nutritional supplement, not only in rodents, but in humans as well by preventing weight loss during a period in the neonate when host defenses are being established.

Example 4

Clinical Trials

Clinical studies were conducted on 76 pediatric patients admitted to the hospital with viral and bacterial infections (Table II). Forty randomly selected patients received lecithin over a period of hospital confinement. Thirty-six patients were given placebo treatment over the same period. Blood was drawn on Day 0, 3, and 7. Lecithin (soy bean lecithin) was administered orally for three consecutive days (3 equal doses per day for a total dose of 450–500 mg/kg/day). Longer periods of administration can be tested; however, the rat studies suggested that three days of administration should have some effect. Twenty-six of the experimental group and 25 of the placebo group had bacterial infections; viral infections in each group numbered 12 and 11, respectively. Admissions from other causes received treatment with lecithin. Natural killer cell activity, as measured by $^{51}$chromium assay and at three different ratios of effector cell to target cell, showed lecithin to be a potent inducer of NK activity in these patients (Tables III, IV, V). Table VI and VII show the findings of phagocytosis and the percent of phagocytosed bacteria (intracellular killing) "killed" in 85 normal individuals of ages ranging from 2 years to 39 years of age. With this assay, approximately 40% of the bacteria are ingested and 85% of these are "killed". It is clear from Tables XI and XII that both phagocytosis and "killing" were enhanced by the administration of lecithin. Analysis of Variance indicated a statistically significant effect of lecithin on NK activity and on phagocytosis and "killing" by PMNs compared to the placebo group. A related finding of increased plasma proteins was seen within the treated group.

An additional child admitted for viral bronchopneumonia had a preexisting retinoblastoma and was treated with lecithin. Within 7 days of the treatment his kill activity was seen to increase from 0–7100 with a concomitant rise in WBC from 2320–5600. The child was discharged 10 days post admission with the pneumonia resolved. This isolated case is mentioned anecdotally and not included in the study data. Nonetheless, we were pleased and impressed with both the clinical outcome of this boy's illness and the laboratory data generated by his admission.

Clearly the dramatic effect of lecithin on the clinical course and outcome of both bacterial and viral infections empirically demonstrates the use and value of this and related molecules.

Example 5

The Effect of PC on Mortality, Bacteremia, White Blood Counts and IgG and IgM in Rats Infected with Klebsiella Pneumoniae Forty-five Wistar rats (five weeks old) were divided into two groups. The experimental group of 25 rats received intraperitoneal injections of PC (800 mg/KG in a 1 ml volume) on Day 0. The control group of 20 rats received equal volume intraperitoneal injections of PBS (pH 7.2) at the same time. On Day 4, both the experimental and the control groups received intravenous injections of $5 \times 10^8$ CFU of *Klebsiella pneumoniae* (K8).

Results

At the end of six days, only 10 of the rats who received PBS were alive compared to 18 alive in the PC group.

One day after the administration of *Klebsiella pneumoniae* (K8) the Colony Forming Units ($Log_{10}$) per ml of blood was approximately 4.2 and slowly fell to 3 by Day 5 in the PBS treated group. The PC group had essentially the same bacterial load on Day 1, but it rapidly decreased to less than one by Day 5. Not only was the bacterial load less in PC treated animals compared to PBS treated rats but so was the clearance. By Day 5, 8 of 9 animals tested in the PC treated group had negative blood cultures compared to 1 of 6 animals in the PBS group.

The neutrophilia induced by K8 increased from about 1000 PMNs/mm$^3$ prior to infection to approximately 3000/mm$^3$ 24 hours later. PC administration resulted in a much greater response and appeared to augment the K8 response by a two and one-half fold increase in circulating PMNs. At the end of six days, there was no difference in PMN counts between the groups (PC vs. PBS). There were no significant changes in IgG or IgM levels in either group during the course of the study. (It should be noted that in a single mouse experiment PC administration resulted in a neutrophilia; PBS and liquid paraffin did not.)

Example 6

Effect of PC on Response of Macrophages to Toxoplasma Gondii Infections

A. Effect of PC on Infection of Murine Macrophages

For four consecutive days, normal CD-1 female mice (8 weeks-old) were inoculated intraperitoneally with PBS (control), high dose PC (10 mg/kg) or low dose PC (5 mg/kg). The mice were sacrificed seven days later. Adherent peritoneal macrophage monolayers prepared from each group were challenged with RH strain toxoplasma tachyzoites (zero time) at a multiplicity of infection ratio of 1:1 (parasite:macrophage). At 1 and 18 hours after zero time, monolayers were fixed and strained, and then assessed for percent infection (number of infected macrophages/total number of macrophages counted (200)×100).

Results

Figure 3:
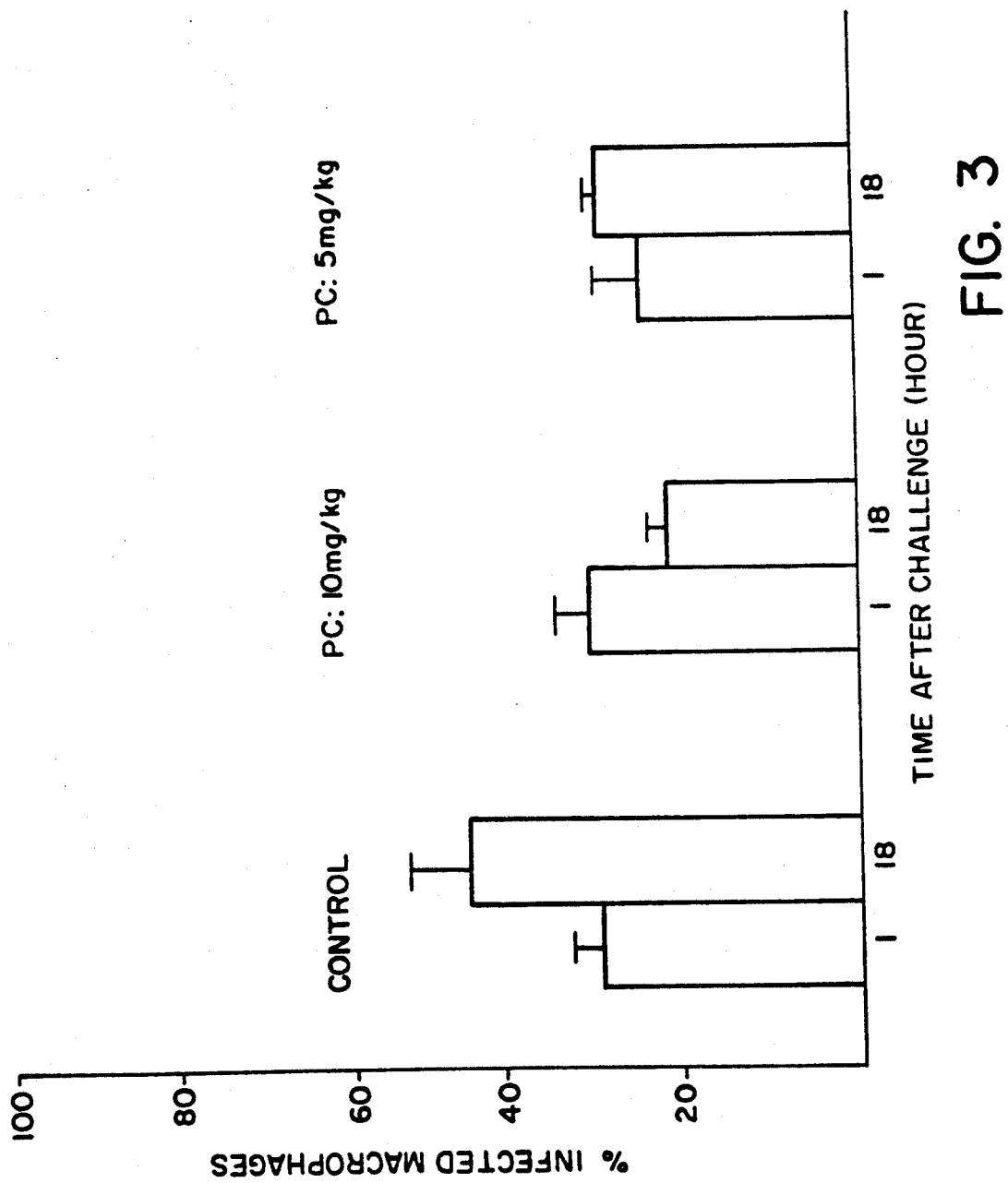
FIG. 3 illustrates the effect of phosphatidyl choline (PC) on infection of murine macrophages.

The percent infection was not significantly different between groups at 1 hour. At 18 hours, however, the percent infection±SD in the control group was significantly higher (P 0.05) than in either the high dose (20.25±1.06) or the low dose (28.5±0.0) PC groups. (See FIG. 3.) (The significance of the differences between test and control groups was assessed by chi-square analysis.)

B. Effect of PC on Intracellular Multiplication of RH Strain Tachyzoites Within Macrophage Vacuoles Mice were treated with either PBS (control), high dose PC (10 mg/kg) or low dose PC (5 mg/kg) according to the protocol outlined in 5 A. Seven days later, macrophage monolayers were prepared from each group, then infected with RH strain tachyzoites (zero time) at a multiplicity of infection ratio of 1:1 (parasite:macrophage). Eighteen hours after zero time, monolayers were fixed, stained and assessed by light microscopy for evidence of intracellular multiplication of toxoplasma within macrophage vacuoles. Data are expressed as the percent of infected macrophages with 0, 1 and 3 parasite divisions per vacuole for each group.

Results

Figure 4:
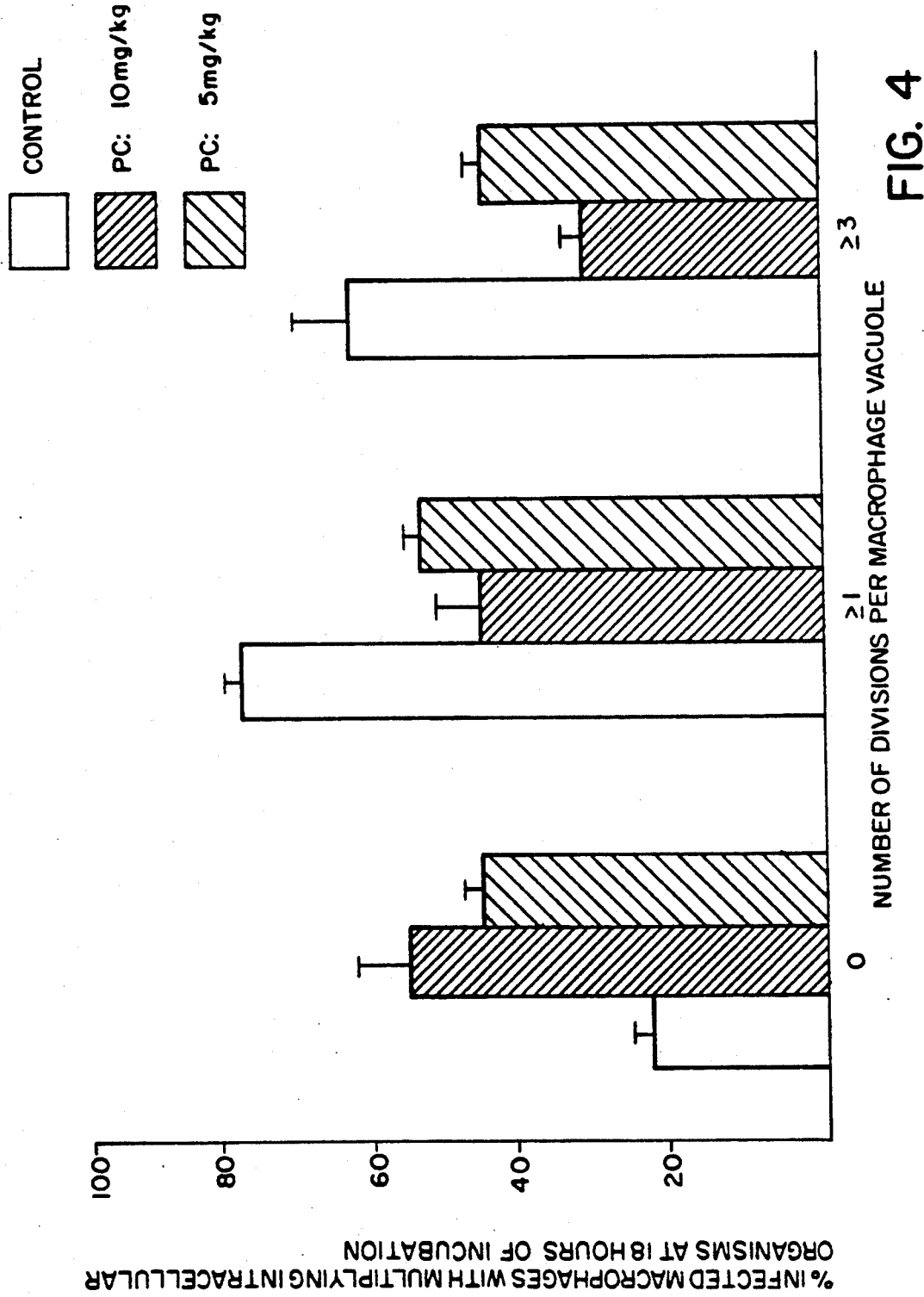
FIG. 4 illustrates the effect of PC on intracellular multiplication of RH strain tachyzoites within macrophage vacuoles.

The control group revealed significantly (P 0.01) fewer percent infected macrophages±SD with no parasite divisions (22.5±0.71) than either the high dose PC group (54.5±6.36) or the low dose PC group (45.5±0.71). However, the control group had significantly (P 0.05) more percent injected macrophages with 1 (77.5±0.71) or 3 (63.00±8.49) parasite divisions compared with the respective values for the high dose PC group (1:45.5±6.36; 3:28.5±3.54) and the low dose PC group (1:54.5±0.71; 3:45.5±2.12). (See FIG. 4.) (The significance of the differences between test and control groups was determined by the t-test for summary data.)

Summary of Example 6

Peritoneal macrophages obtained from CD-1 mice 7 days after treatment with PC either at high dose or low dose exhibited: (a) significantly reduced infection rates 18 hours after in vitro challenge with RH strain toxoplasma tachyzoites compared with the controls, and (b) significantly reduced intracellular replication of the parasite 18 hours after in vitro infection compared with the controls.

These data suggest that in vitro treatment of normal mice with PC has significant direct or indirect effects on enhancement of macrophage microbicidal activity for the parasite in vitro. Since macrophages are the single most crucial element in the cell-mediated immune response to this parasite, the data also suggest that PC treatment may significantly affect the course of acute toxoplasma injection in the normal host as well.

Example 7

The Effect of "Local" Versus "Systemic" PC or PBS on NBT Reduction by Isolated Rat PMNs and Macrophages "Local": Polyvinyl sponges treated with either PBS or PC were implanted under the skin. After 18 hours, the sponges were removed and PMNs isolated. Just prior to sacrifice, PMNs and peritoneal macrophages were isolated from blood. NBT (Nitroblue tetrazolium) Reduction was used to assess microbicidal activity.

"Systemic": Rats were treated with PC or PBS once 4 days prior to sacrifice. Then, 18 hours prior to sacrifice, peritoneal macrophages were isolated by 10 mls of PBS lavage.

Results

Table VIII indicates that circulating PMNs that migrated to the sponge were not affected by the PC and that if PC leaked out of the sponge, it had no effect on PMNs isolated from blood. No differences in NBT reduction by PMNs or macrophages were observed between PC and PBS treatments.

Table IX demonstrates that rats pretreated with PC had significantly more active PMNs and macrophages compared to the PBS treated animals.

Furthermore, as the results are based on a known cell quantity, in PC treated animals the PMNs isolated from the sponge showed significantly greater activity than those isolated from blood.

The same observation holds true for PMNs isolated from the sponge versus those isolated from the blood in PBS treated animals. The difference between the two groups is also statistically significant suggesting that (a) PMNs responding to a foreign substance may not be from the same pool as those circulating in blood; and/or that (b) more active PMNs (and possibly macrophages) are attracted to the site of a foreign body (sic. infection); (c) PC affects different pools of PMN; and (d) PC is acting on PMN precursors.

Example 8

The Effect of Ingested PC by Normal Healthy Young Adults on PMN Function

Seven healthy young adults ages 23-35 were fed 27 grams of PC or a placebo per day in three divided doses for 3 days in a cross-over study. Normally, these individuals would ingest approximately 4 to 6 grams of phospholipids per day, not all of which would be PC derived from soy. Tables X and XI describe briefly the phagocytosis and "killing" assays.

Bloods were drawn on Days 0, 3, 7 and 14 and PMNs isolated according to accepted procedures. Phagocytized *Candida albicans* yeast particles were also determined according to accepted procedures.

Initially, four individuals were fed the PC and three, the placebo. A two week period of nontesting was observed at which time the groups were reversed and those who initially were given PC were given the placebo, and, conversely, the initial placebo-treated group was given PC.

Results

The results for the first part of the study are shown on Tables XII, XIII and XIV. As was anticipated from the Klebsiella experiment, the effect of PC on phagocytosis and "killing" was observed up to 4 days post-ingestion. By Day 14, the enhanced phagocytosis and "killing" was inconsistent. These experiments are being continued to determine more precisely the effects of one feeding versus several, how long the effect lasts, etc.

In summary, PC increases PMN phagocytosis and the percent of phagocytized *Candida albicans* killed.

Effect of PC on Arachidonic Acid Concentrations in PMNs Before and After Exposure to Candida Albicans and Relation to Phagocytosis/Killing Since subjects were fed 4 to 5 times the average intake of lecithin (a lipid), and since lipid is the most abundant material on all cell membranes, it was important to determine if any changes in total lipid or fatty acids occurred in the PMNs of the subjects. The phospholipid used in these studies is PC with a fatty acid composition shown in Table XV. It contains principally linoleic acid (18:2 6) and no arachidonic acid (20:4 6).

Initial studies on screening the fatty acid composition of PMNs isolated from subjects who had injested PC revealed a notable increase in 20:4 with minimal changes in other fatty acids. Since arachidonic acid plays an essential role in the production of several substances, such as vasoactive substances and immune modulators (i.e., prostaglandins and leukotrienes), we decide to assay the 20:4 levels in PMNs of the seven healthy adult subjects fed PC before and after exposure to *Candida albicans* and correlate changes, if any, in 20:4 with the phagocytic and "killing" results (previous section). Assays were done on Day 0 (baseline) and on Days 3 or 4, 7 or 8 and 13 or 14. The subjects reported on in the section entitled "The Effect of Ingested PC by Normal Healthy Young Adults on PMN Function" provided the PMNs making it possible to correlate the changes in phagocytosis and "killing" by PMNs with levels of 20:4 before and after PMN exposure to *Candida albicans*. Fatty acids were extracted from PMNs and assayed by GLC according to published methods.

Figure 5:
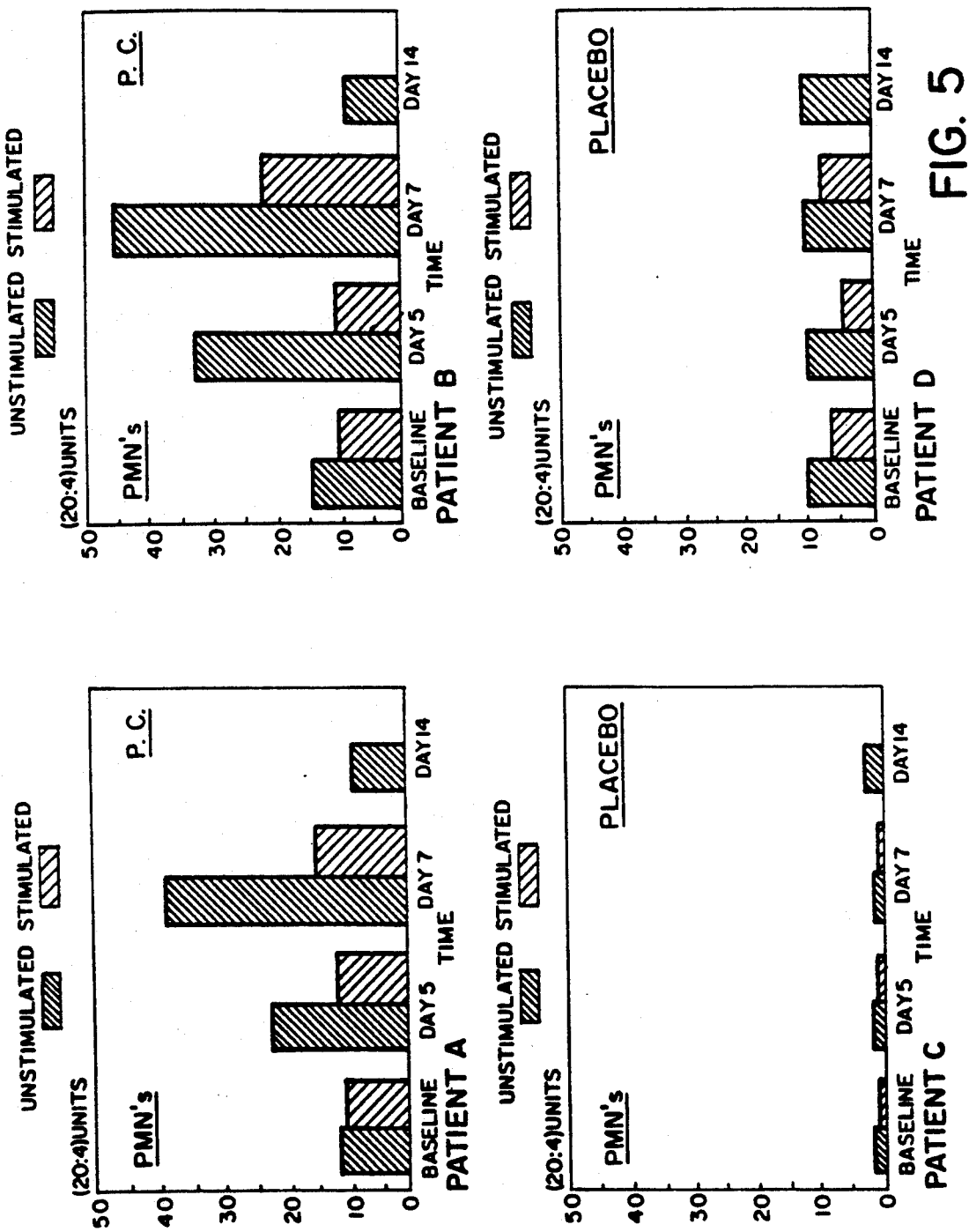
FIG. 5 illustrates the changes in 20:4 of PMNs before (unstimulated) and after (stimulated) exposure to *Candida albicans* in four subjects—two fed PC and two fed placebo.

FIG. 5 depicts the concentration (Units, relevant to a standard) of 20:4 in PMN before (unstimulated) and after (stimulated) exposure to *Candida albicans* ($5 \times 10^3$ PMN to $10 \times 10^6$ *C. albicans*) on Day 0 (baseline), 5, 7 and 14 from four subjects: two fed PC and two fed placebo for only three days. Fatty acid analysis of PMNs showed a 2 fold and a 4 to 5 fold increase in arachidonic acid on Days 5 and 7, respectively, from baseline values in PC group. No changes were noted when the individuals were ingesting the placebo. When these PMNs from PC fed individuals were exposed to *Candida albicans* the arachidonic levels returned to baseline levels. Additional data on seven other subjects is shown in Table XVI. Those results suggested that the enhanced microbicidal effects of PC may be partly mediated through this increase in arachidonic acid which is a precursor of a leukotriene, LTB4, a potent chemoattractant. There is a significant increase in LTB4 release from PMNs isolated from subjects fed PC compared to normal individuals ingesting amounts found in the average American diet. No changes in arachidonic acid were noted in platelets; however, there is a need to look at other cell types (e.g., T and B cells).

Table XVII illustrates the association between the decrease (change) in PMN 20:4 levels after "stimulation" with Candida and the percent of phagocytized Candida killed, the latter data from the previous section (Table XIV).

Example 9

Effects of Soy-Lecithin (PC-95) on Neutrophil (PMN) Killing of Candida Albicans in AIDS Subjects These subjects included 3 males and 4 females who ranged in age from 25 to 45 years old, and who had a history of intravenous drug abuse. At the time of study, 4 subjects were receiving methadone treatment and three subjects were methadone-free. Four of the seven had a documented history of oral candidiasis. The experimental design consisted of the oral administration of 18 grams of PC-95 to subjects in a single dose. PC-95 is a mixture of 95% phosphatidyl choline and 5% phosphatidyl ethanolamine. Blood samples were drawn pre-supplementation, and at 48 hours and 72 hours post-supplementation for analysis of PMN killing of *C. albicans*. The results of assays showed that PMN killing increased significantly over baseline (Table XVIII). In three of four methadone treated and one of three methadone-free subjects, the candidicidal activity increased 48 hours post-supplementation with the remainder of the study population showing the increase in PMN killing capacity 72 hours post-supplementation. PMN killing of Candida increased between 200 and 300 percent in each subject (Table XVIII). In four additional patients not shown in Table XVIII, comparable increases in neutrophil killing of *C. albicans* were observed. These results suggest significant clinical improvement may be obtained by PC-95 supplementation. Given the high recurrence rate of opportunistic infections in AAC and AIDS patients requiring repeated and costly physician visits and hospitalizations, PC-95 may be a promising treatment both for producing clinical improvement and reducing the financial strain on the medical care system.

Example 10

Effects of Oral Soy Phosphatidylcholine Containing Linoleic Acid as the Fatty Acid Constituent on Polymorphonuclear Leukocyte (PMNL) Phagocytosis and Killing of Candida albicans

Subjects

Eight healthy adult volunteers, six males and two females, 23–35 years of age, supplemented their normal diets with either a noodle soup (placebo) or noodle soup to which 27 grams of soy phosphatidylcholine (PC) was added. The PC was 95% phosphatidylcholine and 5% lysophosphatidylcholine; its fatty acid composition is indicated in Table XIX. The placebo or PC was given in three divided servings daily for three days in an open crossover design. Initially, five individuals were fed PC and three placebo.

Following a two week period without supplementation, the groups were reversed. The PC provided approximately 18 grams of linoleic acid and 368 kcal/day. The placebo provide no linoleic acid and 125 kcal/day. Blood was drawn prior to the ingestion of the supplements and than at four, seven and fourteen days after initiation of the supplements. In four of these same subjects, after a two week hiatus, 18 grams of PC were administered in a single feeding and blood was drawn prior to ingestion and at 48 hours post-ingestion for leukotriene B4 (LTB4).

Separate experiments were done in an open design in sixteen healthy adult volunteers after informed consent. Five males and three females, 23-63 years of age, supplemented their normal diets with a single feeding of 18 grams of PC added to noodles.

Six males and two females, 23-63 years of age, supplemented their normal diets with a single feeding of 15 grams of safflower or soybean oil added to noodles. The noodles with PC provided 12 grams of LA and 287 kcal whereas the triglycerides, safflower or soybean oil, provided 12 grams of LA and 260 kcal. Blood was drawn at baseline and at 48 hours post-ingestion.

Analysis

PMNLs were isolated by the method of Boyum, A., Scand J Clin Invest 21: 77-89 (1968), and PMNL phagocytosis was measured by the method of Bridges, C. G., et al., NEED JOURNAL 42: 226-33 (1979), which involves inhibition of H-uridine uptake. PMNL killing of Candida albicans was determined by the method of Levitz, S. M., and Diamond, R. D., J. Infect Dis, 152(5): 938-45 (1985), utilizing the reduction of tetrazolium salt. PMNL lipids were extracted by the Folsch technique, Folsch, J., et al., J. Biol Chem, 226: 497-509 (1957). The addition of an internal standard, L$\alpha$-di-heptadeconylphosphatidylcholine (Avanti Polar Lipids, Birmingham, AL) to the Folsch extract enabled the quantative analysis of the phospholipid fatty acids. Gravimetric analysis of lipid concentration was determined on an automatic electrobalance (Cahn/Ventron, Cerritos, CA) following solvent evaporation. The PMNL lipid extract was then streaked onto a 20×20 cm silica gel-G thin layer plate (Analtech, Inc. Neward, NJ). Thin layer chromatography was performed in a hexane:diethyl ether: glacial acetic acid (70:30:1) solvent system, which separated the major lipid calsses, phospholipids (origin), unesterified cholesterol (rF=0.25), free fatty acids (rf=0.45), triglycerides (rf=0.68) and cholesterol esters (rf=0.085). The phospholipid silica band was then scraped for the transmethylation process, Morrison, W., Lloyd, D. J. Lipid Res, 5: 600-8 (1976). The sample was subjected to 0.5 ml of boron trifluoride reagent (Supelco, Bellfonte, PA); 0.5 ml of fresh methanol (Fisher Scientific, Medford, MA) and then mixed with a Vortex mixer under nitrogen. This solution was heated in a steam bath at 80° C. for one hour to complete transterification, Metcalfe, L. D., Schmitz A. A., Anal. Chem., 33: 363-4, (1961). To stop the reaction, 1 ml of $H_2O$ was added. The fatty acid methyl esters were extracted with $5^2$ ml of hexane (Fisher Scientific, Medford, MA). The hexane was then evaporated under nitrogen in preparation for gas liquid chromatographic (GLC) analysis. Phospholipid fatty acid methyl esters from PMNLs were separated using a Varian Model 3700 capillary gas-liquid chromatograph and a Varian DS-651 chromatographic workstation (Varian Instruments), Palo Alto, CA). The GLC was equipped with a Supelco 2330 fused silica capillary column (30 meters×0.25 mm I.D., 0.2 micron film) and a flame ionization detector (Varian Instruments. The optimal detection conditions were helium carrier gas at a linear velocity of 20 cm/second and a split ratio of 25:1. The capillary column temperature was 190° C. with injector and detector temperatures at 250° C. LTB4 release was measured after exposure of PMNLs to the calcium ionophore, A21387, and to N-formylmethionylleucyl-phenylanine (fMLP) by H radioimmunoassay (Advanced Magnetics, Inc., Cambridge, MA) according to the method of Salmon, et al., A Radioimmunoassay for Leukotriene B4. Prostaglandins, 24(2): 225, (1982), Palmer, R. M. J., Salmon, J. A., Immunology, 50: 65-73, (1983).

Statistics were done utilizing Student t-tests, analysis of variance for four repeated measures and two independent groups, and Pearson correlations, Colton, T., Statistics in Medicine. Boston: Little-Brown, (1974).

Results

Neutrophil Function

Phagocytosis by PMNLs from subjects provided 27 grams of PC for three days increased 1.6 fold ($p<0.01$) at four days, peaked at 2.0 fold ($p<0.01$) times baseline seven days post-ingestion, and returned to baseline values at day fourteen (Table XX). Similarly, PMNL killing increased 2.6 fold ($p<0.01$) to peak by day four in the PC group, and returned nearly to baseline at fourteen days post-ingestion (Table XX). Compared with the subjects provided placebo, the increase in phagocytosis by PMNLs from the PC group was highly significant at days four and seven whereas killing was significantly increased at days four, seven and fourteen post-ingestion.

The results observed on study day four, one day after the last of three days of feeding 27 grams of PC per day, raised the issue as to whether the effects of three days of feeding PC were required for the observed effects or whether similar results in PMNL function could be observed after a single feeding. Also, were an effect observed after a single feeding, the question was raised as to the minimal time interval for an effect after a single dose.

In a preliminary experiment in which multiples of 9 grams of PC were given to eight subjects and bloods drawn at 24 hour intervals, it was found that 18 grams of PC providing 12 grams of LA was the minimal dose and 48 hours was the minimal time interval in which an increase in PMNL killing was observed (Table XXI).

Arachidonic Acid Composition of Neutrophil Phospholipids

The phospholipid arachidonic acid (PL-AA) content of PMNLs from the group fed 27 grams of PC increased 2.9 to 3.7 fold at four and seven days, respectively, post-PC ingestion (Table XX). A smaller, albeit significant, increase of 1.3 fold, was noted 48-hours post-ingestion of 18 grams of PC (Table XXI). Compared with the groups fed placebo or an equal amount of linoleic acid as safflower or soy oil the increases in PL-AA of PMNLs from the PC groups were highly significant at 48 hours (Table XXI). No significant changes were noted in the triglyceride fed groups at four or seven days post ingestion (Table XX).

Arachidonic Acid Release

The PL-AA release from PMNLs stimulated with Candida albicans, increased 3.2 times that at base-line ($p<0.01$) at day four post PC ingestion, with a peak release of 5.3 times baseline ($p<0.001$) at day seven (Table XX). Forty-eight hours after a single 18 gram dose of PC, PL-AA release increased 1.5 times baseline (Table XXI). There were no significant changes in PL-AA release from PMNLs of placebo treated (Table XX) or safflower and soy oil treated subjects (Table XXI). Both PMNL phagocytosis and killing of *Candida albicans* were highly correlated (r=0.872 and r=0.932, respectively), with PMNL PL-AA release.

Generation of the 5-Lipoxygenase Metabolite LTB4

In response to calcium ionophore, A21387, LTB4 generation from PMNLs of the subjects fed the 18 grams of PC increased from 14.5 to 56.2 pg/($10^5$ PMNL) at 48 hours. In response to fMLP, LTB4 increased from <0.05 pg/($10^5$ PMNL) to 98.75 pg/($10^5$ PMNL), (Table XXII). The PMNLs from one non-supplemented subject showed no increase in LTB4 generation when stimulated with either A21387 or fMLP.

Conclusions

The results of these studies on humans and animals indicate that the administration or ingestion of PC (1) has long lasting effects, at least up to 4 days or longer post feeding or administration; (2) has beneficial effects in both children with bacterial and viral infections and in animals made septic; (3) is effective in the prevention and treatment of neonatal morbidity and mortality due to *T. gondii, K. pneumoniae, C. albicans* and streptococcal infections and thus to other bacterial, viral and protozoan infections; (4) increases the level of PMN arachidonic acid, presumably in the membrane, and that the enhancement of microbicidal activity of PMNs and macrophages seen in animals and humans fed PC is likely due to an increase in the precursor, arachidonic acid, of the leukotriene, LTB4; and (5) increases PMN and macrophage microbicidal activity as well as cellular and humoral responses. Dietary lipids and/or cholesterol in various quantitative and qualitative levels can alter the composition of the lipid membrane of all cells resulting in changes in structure and function. Knowing the rate at which cells differentiate, proliferate and depending on their half-life, the lipid composition of host defense cells can be altered by proper dosing (feeding) with PC, qualitatively and quantitatively, causing them to be more active resulting in lessening the morbidity and mortality of bacterial and viral infections in animals and humans. Furthermore, the data demonstrates that we can enhance the production of a leukotriene, LTB4, as well as enhance phagocytosis and intracellular killing by polymorphonuclear leucocytes and macrophages.

As with most intracellular pathogens—including HIV (AIDS virus)—replication, and thus severity of disease, occurs within the cell by altering receptor sites, rigidity (or fluidity) and function of cells. For example, the malaria parasite replicates within the red cells by causing perturbations in the lipid membrane of the RBC both in a qualitative and quantitative sense as does *Toxoplasma gondi* in macrophages. Macrophages play a key role in amplifying both cell mediated and humoral responses to infection and in disposing of foreign and infected cells.

These studies suggest that PC can diminish/suppress the conversion of AIDS positive individuals to clinical disease.

Equivalents

Those skilled in the art will recognize, or be able to ascertain, using no more than routine experimentation, numerous equivalents to the specific substances and procedures described herein. Such equivalents are considered to be within the scope of this invention, and are covered by the following claims.

TABLE I

WEIGHT GAIN IN NEWBORN WISTAR RATS TREATED WITH PHOSPHATIDYL-CHOLINE (MEAN ± S.D. GRAMS)

| | TREATMENT (SINGLE DOSE ip) | | |
|---|---|---|---|
| DAY | PBS CONTROL (n:6) | P.C. 95 (n:7) | p |
| 0 | 8.6 ± 0.3 | 9.1 ± 0.4 | NS |
| 2 | 9.8 ± 0.3 | 10.4 ± 0.6 | NS |
| 5 | 11.9 ± 0.4 | 12.4 ± 0.4 | NS |
| 7 | 14.9 ± 0.5 | 15.4 ± 0.4 | NS |
| 9 | 17.9 ± 0.8 | 18.7 ± 0.7 | NS |
| 11 | 20.5 ± 0.7 | 21.1 ± 0.8 | NS |
| 14 | 20.2 ± 1.0 | 31.2 ± 0.7 | 0.001 |
| 16 | 21.9 ± 1.1 | 35.8 ± 1.1 | 0.001 |
| 19 | 24.3 ± 1.2 | 39.1 ± 1.1 | 0.001 |
| 50 | 123.0 ± 6.5 | 151.0 ± 16.4 | 0.01 |

TABLE II

CLINICAL AND LABORATORY CHARACTERISTICS OF STUDY GROUPS ON ADMISSION

| | Protocol | |
|---|---|---|
| Characteristics | Lecithin | Placebo |
| No. of Patients | 40 | 36 |
| Male | 21 | 19 |
| Female | 19 | 17 |
| Age (months) | | |
| Mean ± S.E. | 66 ± 11.3 | 40 ± 9.13 |
| Range | 5-192 | 6-180 |
| Fever: mean °C ± S.E. | 33.31 ± 0.14 | 38.53 ± 0.14 |
| Total WBC ± S.E | 12,203 ± 1,490 | 15,668 ± 1,453 |
| Infections: | | |
| Bacterial | 26 | 25 |
| Viral | 12 | 11 |
| Other | 2 | 0 |

TABLE III

NATURAL KILLER CELL ACTIVITY IN 60 CHILDREN WITH INFECTION (Effector: Target* ratio 50:1)

| | % Killing ± S.E. | | |
|---|---|---|---|
| Group: | Day 0 | Day 3 | Day 7 |
| Placebo n = 30 | 19.78 ± 1.10 | 18.33 ± 1.18 | 20.09 ± 1.16 |
| PC n = 30 | 18.89 ± 1.09 | 26.01 ± 1.15 | 28.78 ± 1.52 |
| Control n = 30 | | 20.67 ± 1.69 | |

*Target K562 16-hour $^{51}$Cr release assay.

TABLE IV

NATURAL KILLER CELL ACTIVITY IN 60 CHILDREN WITH INFECTION (Effector: Target* ratio 25:1)

| | % Killing ± S.E. | | |
|---|---|---|---|
| Group: | Day 0 | Day 3 | Day 7 |
| Placebo n = 30 | 13.42 ± 0.89 | 13.19 ± 0.75 | 14.03 ± 0.80 |
| PC n = 30 | 13.61 ± 0.76 | 20.96 ± 1.33 | 22.49 ± 1.29 |
| Control n = 30 | | 13.85 ± 1.35 | |

*Target K562 16-hour $^{51}$Cr release assay.

TABLE V
NATURAL KILLER CELL ACTIVITY IN 60 CHILDREN WITH INFECTION
(Effector: Target* ratio 12.5:1)

| Group: | % Killing ± S.E. | | |
|---|---|---|---|
|  | Day 0 | Day 3 | Day 7 |
| Placebo n = 30 | 8.95 ± 0.84 | 8.56 ± 0.88 | 10.12 ± 1.04 |
| PC n = 30 | 8.91 ± 0.78 | 14.89 ± 1.30 | 15.44 ± 1.16 |
| Control n = 30 |  | 10.64 ± 1.19 |  |

*Target K562 16-hour $^{51}$Cr release assay.

TABLE VI
PHAGOCYTIC ACTIVITY AND INTRACELLULAR KILLING BY PMNs FROM NON-INFECTED NORMALS*

| No. of Subjects | Percent ± S.E. | |
|---|---|---|
|  | Phagocytosis | Intracellular Killings |
| n = 85 | 43.73 ± 1.73 | 85.61 ± 1.94 |

*$^3$H-Uridine Assay in Mexican study population.
Staphylococcus aureus: PMN ratio, 5:1

TABLE VII
PHAGOCYTIC ACTIVITY OF PMNs AS ASSESSED BY THE $^3$H-URIDINE UPTAKE INHIBITION ASSAY*

| Group: | % Phagocytosis ± S.E. | | |
|---|---|---|---|
|  | Day 0 | Day 3 | Day 7 |
| Placebo n = 36 | 33.45 ± 2.85 | 30.63 ± 2.55 | 28.82 ± 1.67 |
| PC n = 40 | 31.98 ± 2.48 | 42.40 ± 2.31 | 36.02 ± 2.58 |
| Control n = 85 |  | 46.73 ± 1.73 |  |

*Staphylococcus aureus: PMN ratio, 5:1
AB serum used
Mexican study population

TABLE VIII
EFFECT OF "LOCAL" PC OR PBS ON NBT REDUCTION BY ISOLATED RAT PMNs AND MACROPHAGES

| White Cell | Source | NBT Reduction (O.D.) (1.5 × 10⁶ cells) | | | |
|---|---|---|---|---|---|
|  |  | PC* (6 rats) | | PBS* (6 rats) | |
| PMNs | Blood | .065 (.011) | (ns) | .052 (.011) |  |
| PMNs | Sponge | 0.083 (.019) | (ns) | .047 (.012) |  |
| Macrophages | Peritoneal | 0.238 (.043) | (ns) | .244 (.062) |  |

*0.5 ml PC (5 mg)
PBS/sponge (implanted - 18 hrs)
**Peritoneal macrophages obtained prior to sacrifice with 10 ml PBS lavage (i.p.)

TABLE IX
EFFECT OF PC OR PBS ON NBT REDUCTION BY ISOLATED RAT PMNs AND MACROPHAGES

| White Cell | Source | NBT Reduction (O.D.) PC-i.p. - PBS | | |
|---|---|---|---|---|
| PMNs | Blood | .074 (.012) | sig. | .038 (.010) |
| PMNs | Sponge | 0.132 (.015) | sig. | .079 (.009) |
| Macrophages | Peritoneal | 0.160 (.011) | sig. | .112 (.011) |

NBT Reduction - Mean (± S.E.) (1.5 × 10⁶ cells)
PC (1 ml) 800 mg/Kg or PBS (1 ml) on day 4: Sponge implanted - 18 hrs
Peritoneal cells obtained prior to sacrifice with 10 ml of PBS lavage (i.p.)
P = <.05

TABLE X
PHAGOCYTOSIS
PMN (2.0 × 10⁵) and C. albicans (5 × 10⁵)

| Blanks (2) | C. albicans | PMNs & C. albicans |
|---|---|---|
| (a) media |  |  |
| (b) PMNs |  | Incubate 1 hour (add) |
| <1% CMP |  | $^3$H-Uridine (30') Harvest cells count |

Phagocytized C. albicans do not take up label and do not adhere

TABLE XI
"KILLING" ASSAY

| PMN (2.5 × 10⁵) C. alb. (5 × 10⁵) | PMN and Heat "killed" C. albicans | Viable C. albicans |
|---|---|---|

Incubate 1 hour
Wash (3×)
300 ul H2O
Centrifuge-Resuspend (NTB)-(incubate 3 hrs)-Centrifuge
Pellet - add 400 ul HCl/Isopropyl alcohol
Mix - read at O.D. 570

(live C. albicans converts NTB - blue color)

TABLE XII
Phagocytosis (%) of Candida albicans* by PMNs from Healthy Adults Fed Phosphatidyl Choline for Three Days**

| Days: | 0 | 3-4 | 7-8 |
|---|---|---|---|
| PC (4) | 34.5 (23-56) | 43.5 (32-55) | 60.0 (52-74) |
| Placebo (3) | 30.7 (22-32) | 32.3 (31-33) | 21.7 (16-27) |

*PMN/C. albicans - 2.5 × 10⁶/5 × 10⁶
**27 g PC/day/3 days

TABLE XIII
Killing (%) of Candida albicans* by PMNs from Health Adults Fed Phosphatidyl Choline for Three Days**

| Days | 0 | 3-4 | 7-8 |
|---|---|---|---|
| PC (4) | 19 (15-22) | 40.2 (28-60) | 38.2 (31-43) |
| Placebo (3) | 35 (10-52) | 24.7 (11-46) | 31.7 (21-44) |

*PMN/C. alb. - 2.5 × 10⁶/5 × 10⁶
**27 g PC/day/3 days

TABLE XIV
Percent of Phagocytized C. albicans* Killed by PMNs Isolated from Healthy Adults Fed Phosphatidyl Choline for Three Days**

| Days: | 0 | 3-4 | 7-8 |
|---|---|---|---|
| PC (4) | 6.3 (3.9-8.4) | 17.8 (11.9-31.8) | 22.8 (18.0-29.6) |
| Placebo (3) | 10.4 (3.2-16.7) | 8.0 (3.6-15.2) | 8.4 (4.8-10.2) |

*PMN/C. albicans - 2.5 × 10⁶/5 × 10⁶
**27 g PC/day/3 days

TABLE XV
FATTY ACID COMPOSITION OF SOY LECITHIN

| FATTY ACID | SOY LECITHIN (% weight) |
|---|---|
| 16:0 | 12.8 |
| 16:1w7 | 0.2 |
| 18:0 | 2.9 |
| 18:1w6 | — |
| 18:1w9 | 10.6 |
| 18:2w6 | 65.9 |
| 18:3w3 | 6.5 |
| 20:1w9 | 0.2 |
| 20:4w6 | — |
| 20:5w3 | — |

TABLE XVI
Effect of Oral PC on Arachidonic Acid (20:4) Levels of PMNs and After Exposure to *Candida albicans*

| Days | 0 | 3-4 | 7-8 |
|---|---|---|---|
| PC (4) | | | |
| Before | 6.4 (3.1-9.0) | 10.4 (3.8-20.6) | 17.3 (5.7-29.1) |
| 20:4 (Units) Change | -3.9 (2.3-6.2) | -8.6 (2.7-15.9) | -15.3 (4.8-28.6) |
| Placebo (3) | | | |
| Before | 4.1 (3.2-5.8) | 2.6 (1.8-3.3) | 2.6 (1.9-3.7) |
| 20:4 (Units) Change | -2.6 (1.4-4.1) | -1.8 (1.3-1.5) | -1.9 (1.5-2.5) |

TABLE XVII
Association Between Δ20:4 and Percent of Phagocytized *Candida albicans* Killed (% P/K)

| Days | 0 | 3-4 | 7-8 |
|---|---|---|---|
| PC (4) | | | |
| % P/K | 6.3 | 17.8 | 22.8 |
| Δ 20:4 | -3.9 | -8.6 | -15.3 |
| Placebo (3) | | | |
| % P/K | 10.4 | 8.0 | 8.4 |
| Δ 20:4 | -2.6 | -1.8 | -2.6 |

TABLE XVIII
THE EFFECTS OF SOY LECITHIN (PC 95) ON NEUTROPHIL KILLING OF *CANDIDA ALBICANS* IN SEVEN HIV POSITIVE PATIENTS

| DAYS | BASELINE | 48 HOURS | 72 HOURS |
|---|---|---|---|
| SUBJECT 1 | 10.4% | 22.2% | 16.5% |
| SUBJECT 2 | 16.3% | 32.1% | 20.4% |
| SUBJECT 3 | 11.8% | 36.6% | 18.3% |
| SUBJECT 4 | 8.0% | 24.9% | 14.5% |
| SUBJECT 5 | 19.6% | 20.3% | 55.7% |
| SUBJECT 6 | 47.9% | 53.2% | 57.1% |
| SUBJECT 7 | 31.6% | 25.1% | 56.7% |

* percent killing of *C. albicans* by MTT reduction.

TABLE XIX
THE FATTY ACID COMPOSITION OF SOY PHOSPHATIDYLCHOLINE

| FATTY ACID | PERCENT |
|---|---|
| Palmitic (16:0) | 12.8 |
| Palmitoleic (16:1 n7) | 0.2 |
| Stearic (18:0) | 2.9 |
| Oleic (18:1 n9) | 10.6 |
| Linoleic (18:2 n6) | 65.9 |
| Linolenic (18:3 n3) | 6.5 |
| Eicosenoic (20:1 n9) | 0.2 |
| Arachidonic (20:4 n6) | — |
| Eicosapentaenoic (20:5 n3) | — |

TABLE XX
EFFECTS OF OR AL PHOSPHATIDYLCHOLINE ON NEUTROPHIL FUNCTION AND ARACHIDONATE IN NORMAL ADULTS*

| | Phagocytosis of *Candida albicans* (%) | | Killing of *Candida albicans* (%) | | Arachidonic acid levels (ng/$10^5$ PMNL) | | Arachidonic acid release (ng/$10^5$ PMNL) | |
|---|---|---|---|---|---|---|---|---|
| Days | Placebo | PC | Placebo | PC | Placebo | PC | Placebo | PC |
| 0 | 25.8 ± 4.1 | 29.3 ± 4.5 | 15.6 ± 2.7 | 16.0 ± 1.2 | 35 ± 8 | 38 ± 11 | 25 ± 8 | 23 ± 7 |
| 4 | 32.1 ± 2.9 | 48.0 ± 54. § | 20.2 ± 4.9 | 42.1 ± 4.9 § | 29 ± 11 | 109 ± 25 § | 17 ± 8 | 74 ± 16 § |
| 7 | 27.4 ± 4.0 | 59.4 ± 5.2 § | 19.7 ± 4.3 | 39.9 ± 3.7 § | 19 ± 3 | 142 ± 26 ‖ | 10 ± 3 | 123 ± 26 ‖ |
| 14 | 31.4 ± 3.4 | 33.0 ± 3.9 | 11.0 ± 1.4 | 18.6 ± 1.4§ | 17 + 3 | 42 ± 7 | 8 ± 3 | 17 ± 3 |

*N = 8; PC, soy phosphatidylcholine; Values expressed as mean ± SEM
PMNL/*Candida albicans* = 2.5 × $10^6$/5 × $10^6$
P < 0.01 vs. baseline
P < 0.001 vs. baseline
§P < 0.01 vs. placebo
‖P < 0.001 vs. placebo

TABLE XXI
EFFECTS OF PHOSPHATIDYLCHOLINE OR TRIGLYCERIDE (SAFFLOWER OR SOYBEAN OIL) ON NEUTROPHIL KILLING OF *Candid albicans* AND ARACHIDONATE LEVELS*.

| | Killing of *Candida albicans* (%) | | Arachidonic acid levels (ng/$10^5$ PMNL) | | Arachidonic acid release (ng/$10^5$ PMNL) | |
|---|---|---|---|---|---|---|
| | SO | PC | SO | PC | SO | PC |
| Baseline | 24.6 ± 4.4 | 21.2 ± 4.1 | 28 ± 6 | 29 ± 3 | 20 ± 8 | 21 ± 7 |
| 48 hours | 18.2 ± 1.8 | 36.8 ± 3.7 | 22 ± 3 | 39 ± 3 | 19 ± 3 | 31 ± 4 |

*Both phosphatidylcholine and triglycerides provided 12 grams linoleic acid; N = 8 normal adults; SO, safflower oil or soybean oil; PC, phosphatidylcholine. Values expressed as mean ± SEM.
PMNL/*C. albicans* = 2.5 × $10^6$/5 × $10^6$
P < 0.01 vs. baseline

TABLE XXII

GENERATION OF LEUKOTRIENE B4 BY NEUTROPHILS IN RESPONSE TO CALCIUM IONOSPHORE, A21387, AND fMLP*

|  | A21387 (n = 4) | fMLP (n = 4) |
|---|---|---|
|  | (pg/10⁵ cells) | |
| Baseline | 14.5 ± 5.6 | <0.05 |
| PC - 48 hours | 56.2 ± 21.4 | 98.75 ± 33.9 |

*fMLP, N-formyl-methionyl-leucyl-phenylalanine; PC, phosphatidyl-choline provided as a single dose 18 grams; Values expressed as mean ± SEM.
$P < 0.01$ vs baseline.
$P < 0.01$ vs baseline.

I claim:

1. A method of therapy to combat opportunistic viral, bacterial, protistan or yeast infections in an AIDS patient, comprising administering to said AIDS patient an effective prophylactic amount of phosphoglyceride selected from the group consisting of phosphatidylcholine, phosphatidylethanolamine, phosphatidylserine and phosphatidylinositol, or mixtures thereof, sufficient against an infection, the phosphoglyceride containing linoleic acid as the primary fatty acid constituent.

2. A method of claim 1, wherein the infection is a yeast infection.

3. A method of claim 2, wherein the yeast is *Candida albicans*.

4. A method of therapy or prophylaxis of a viral, protistan, bacterial or yeast infection in a patient, comprising administering to the patient with said infection or susceptible to said infection an amount of phosphoglyceride containing linoleic acid as the primary fatty acid constituent, sufficient to stimulate phagocytosis by polymorphonuclear leukocytes.

5. A method of claim 4, wherein the patient has Acquired Immune Deficiency Syndrome (AIDS).

6. A method of claim 4, wherein the phosphoglyceride is selected from the group consisting of phosphatidycholine, phosphatidylethanolamine, phosphatidylserine and phosphatidylinositol, or mixtures thereof.

7. A method of therapy to combat opportunistic viral, bacterial, protistan, or yeast infections in an AIDS patient, comprising administering to said AIDS patient an effective prophylactic amount of a species of phosphatidylcholine in which linoleic acid is the primary fatty acid constituent.

8. A method of claim 7 wherein the infection is a yeast infection.

9. A method of claim 8 wherein the yeast is *Candida albicans*.

10. A composition for treatment of an infection, consisting essentially of an essentially pure phosphatidylcholine in which an omega-6 fatty acid is the only fatty acid constituent and a physiologically-acceptable vehicle.

11. A composition of claim 10, wherein the omega-6 fatty acid is linoleic acid.

* * * * *